(12) United States Patent
Ho et al.

(10) Patent No.: US 8,841,592 B1
(45) Date of Patent: Sep. 23, 2014

(54) SOLAR GLARE HAZARD ANALYSIS TOOL ON ACCOUNT OF DETERMINED POINTS OF TIME

(71) Applicant: Sandia Corporation, Albuquerque, NM (US)

(72) Inventors: Clifford K. Ho, Albuquerque, NM (US); Cianan Alexander Sims, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 204 days.

(21) Appl. No.: 13/626,617

(22) Filed: Sep. 25, 2012

Related U.S. Application Data

(63) Continuation-in-part of application No. 13/240,995, filed on Sep. 22, 2011, now Pat. No. 8,669,509.

(51) Int. Cl.
*G01C 21/02* (2006.01)
(52) U.S. Cl.
USPC ........................................ 250/203.4; 250/205
(58) Field of Classification Search
USPC ................. 250/203.4, 205, 214 R, 214.1; 359/601–605; 136/246; 126/573–578
See application file for complete search history.

(56) References Cited

U.S. PATENT DOCUMENTS

| | | | |
|---|---|---|---|
| 8,716,644 B2* | 5/2014 | Wu et al. ................... | 250/208.2 |
| 2010/0006087 A1 | 1/2010 | Gilon et al. | |

OTHER PUBLICATIONS

Mavis, C.L., 1988, "10 MWe Solar Thermal Central Receiver Pilot Plant Heliostat and Beam Characterization System Evaluation Nov. 1981-Dec. 1986," SAND87-8003, Sandia National Laboratories, Livermore CA, pp. 1-218.

Strachan, J.W. And R.M. Houser, "Testing and Evaluation of Large-Area Heliostats for Solar Thermal Applications," SAND92-1381, Sandia National Laboratories, Albuquerque, NM, 1993, pp. 1-70.

Blackmon, J.B., "Development and Performance of a Digital Image Radiometer for Heliostat Evaluation at Solar One," J. Solar Energy Engr., 107, 1985, pp. 315-321.

Johnston, G., "Focal Region Measurements of the 20 m2 Tiled Dish at the Australian National University," Solar Energy, 63(2), 1998, pp. 117-124.

Ulmer, S., W. Reinalter, P. Heller, E. Lupfert, and D. Martinez, "Beam Characterization and Improvement with a Flux Mapping System for Dish Concentrators," J. Solar Energy Engr., 124, 2002, pp. 182-188.

Slack, M., P. Meduri, and A. Sonn, "eSolar Power Tower Performance Modeling and Experimental Validation," in Proceedings of SolarPACES 2010, Perpignan, France, Sep. 21-24, 2010, pp. 1-8.

(Continued)

*Primary Examiner* — Que T Le
(74) *Attorney, Agent, or Firm* — Medley Behrens & Lewis LLC

(57) ABSTRACT

Technologies pertaining to determining when glare will be perceived by a hypothetical observer from a glare source and the intensity of glare that will be perceived by the hypothetical observer from the glare source are described herein. A first location of a potential source of solar glare is received, and a second location of the hypothetical observer is received. Based upon such locations, including respective elevations, and known positions of the sun over time, a determination as to when the hypothetical observer will perceive glare from the potential source of solar glare is made. Subsequently, an amount of irradiance entering the eye of the hypothetical observer is calculated to assess potential ocular hazards.

20 Claims, 10 Drawing Sheets

(56) References Cited

OTHER PUBLICATIONS

Yogev, O., P. Gleckman, and M. Rozler, 2009, "High-Heat Solar Flux Scanner," in Proceedings of SolarPACES 2009, Berlin, Germany, Sep. 15-18, 2009, pp. 1-8.

Naor, G., G. Goldwine, R. Hayut, O. Bibi, E. Silberstein, O. Chernin, Z. Auman, G. Kroyzer, and A. Ziskin, 2010, "Flux Measurement System Using IR Camera," in Proceedings of SolarPACES 2010, Perpignan, France, Sep. 21-24, 2010, pp. 1-6.

"Topaz Solar Farm Reflection Study", retrieved at <<http://www.slocounty.ca.gov/Assets/PL/Optisolar-Topaz+Solar+Farm/Documents/Application+Submittal+$!232/Attachment+C+-+Topaz+Solar+Farm+Reflection+Study.pdf>>, Feb. 24, 2009, pp. 1-10.

* cited by examiner

US 8,841,592 B1

SOLAR GLARE HAZARD ANALYSIS TOOL ON ACCOUNT OF DETERMINED POINTS OF TIME

RELATED APPLICATIONS

This application is a continuation-in-part of U.S. patent application Ser. No. 13/240,995, filed on Sep. 22, 2011, and entitled "MOBILE COMPUTING DEVICE CONFIGURED TO COMPUTE IRRADIANCE, GLINT, AND GLARE", which is a continuation-in-part of U.S. patent application Ser. No. 13/106,686, filed on May 12, 2011, and entitled "COMPUTATION OF GLINT, GLARE, AND SOLAR IRRADIANCE DISTRIBUTION". The entireties of these applications are incorporated herein by reference.

STATEMENT OF GOVERNMENTAL INTEREST

This invention was developed under Contract DE AC04-94AL85000 between Sandia Corporation and the U.S. Department of Energy. The U.S. Government has certain rights in this invention.

BACKGROUND

Due to environmental concerns pertaining to the use of fossil fuels in connection with generating electric power, including the non-renewability of such fossil fuels and carbon emissions and other pollutants generated when fossil fuels are burned, an increasing amount of research and funding has been directed towards systems that utilize renewable energy resources to generate power. These systems include solar power plants, wind turbines, geothermal power systems, and the like. An exemplary solar power system is a solar power tower (which can also be referred to as a central tower power plant, a heliostat power plant, or a power tower). A solar power tower utilizes an elevated central receiver to collect focused solar radiation from a plurality of reflectors, such as heliostats (mirrors). Solar radiation is reflected from the reflectors and concentrated at the central receiver where a fluid is heated. The heating of the fluid can cause a turbine to be driven to generate electric power. Another exemplary solar power system includes arrays of photovoltaic modules that are configured to convert solar radiation to electric energy. Photovoltaic modules are often installed on rooftops of structures, and in some installations, include numerous modules such that a field of photovoltaic modules is employed to generate electric energy.

It is recognized that mirrors and photovoltaic modules are composed of reflective materials, such that solar radiation that impacts these devices reflects therefrom, potentially directing the irradiance to an eye of a human being. In some instances, irradiance perceived by an observer can be sufficient to, for example, temporarily or permanently impair vision of the observer, which can further lead to undesired consequences. For example, it is undesirable to impair the vision of a motorist, airplane pilot, or the like. When designing buildings, solar power installations, etc., it is therefore desirable to take into consideration potential hazards of glint and glare, wherein glint can be defined as a momentary flash of light, while glare can be defined as a more continuous source of excessive brightness relative to ambient lighting.

Conventionally, to assess potential glare hazards, consultants analyze the geometry of the proposed solar installation system relative to key observation points. Regions where glare can occur at various times throughout the year are analyzed, but no indication of the intensity of glint or glare and their potential ocular impact are provided. In addition, the Sun is treated as a collimated light source (laser beam) with no spreading of the light rays caused by either the size of the Sun or from surface scattering during reflection.

SUMMARY

The following is a brief summary of subject matter that is described in greater detail herein. This summary is not intended to be limiting as to the scope of the claims.

Described herein are various technologies pertaining to assessment of potential glare hazard perceived by a hypothetical observer, wherein the potential glare hazard is caused by a potential source of solar glare. The potential source of glare may be, for example, a solar power installation or a proposed solar power installation, and can include a photovoltaic module, a mirror, glass, or a solar thermal receiver. In another exemplary embodiment, the potential source of glare may be a proposed building that includes reflective material, such as glass.

With more specificity, first location data that is indicative of a first geographic location of a potential source of glare can be received. For example, this first location data can be received by way of a web-based interface that employs an interactive map, such that a user can indicate the first geographic location of the potential source of glare by way of interaction with the interactive map. Furthermore, a value that is indicative of the reflectivity of the potential source of the glare can be received, wherein such value corresponds to a material from which the potential source of glare is composed. Additionally, second location data that is indicative of a second geographic location of a hypothetical observer of the glare is received. Again, for instance, the user can employ the interactive map to relatively easily specify the second geographic location of the hypothetical observer through, for instance, utilization of a mouse or touch sensitive display. Additional information pertaining to the potential source of glare can also be received, including, but not limited to, orientation (azimuth angle) of modules in the potential source of glare relative to a reference orientation, a tilt angle of the potential source of glare relative to a reference plane, elevation of the potential source of glare, and subtended angle of the Sun at the first geographic location. Additionally, details pertaining to the hypothetical observer can be received, including, for instance, a travel path of the hypothetical observer (e.g., along a roadway, a flight path of an airplane), elevation of the hypothetical observer, data pertaining to the eye of the hypothetical observer (e.g., pupil diameter), and the like.

Moreover, a range of time that is desirably considered when analyzing potential glare hazard corresponding to the potential source of solar glare can be received. Such range of time, for instance, can be a week, a month, a year, etc. Through a vector-based analysis, points in time in the time range when the hypothetical observer at the second geographic location will perceive glare from the potential source of glare can be determined. Generally, as positions of the Sun in the sky at points in time throughout the year are known, tilt and orientation of the potential source of glare are known, and geographic positions of the potential source of glare and the hypothetical observer, respectively (including elevations thereof), are known, a vector-based analysis can be undertaken to identify points in time in the time range when the hypothetical observer will perceive glare from the potential source of glare.

Responsive to determining when the hypothetical observer will perceive glare from the potential source of glare, a further analysis can be undertaken to compute intensity of the solar glare as perceived by the hypothetical observer. Such intensity can be a function of the reflectivity of the potential source of glare, distance between the potential source of glare and the hypothetical observer, and features of the human eye. A value that is indicative of intensity of glare perceived by the hypothetical observer is, therefore, indicative of an amount of solar irradiance entering the eye of the hypothetical observer at the second geographic location and is thus indicative of the potential ocular hazard for the hypothetical observer.

Subsequent to computing the values that are indicative of intensities of glare perceived by the hypothetical observer at the second geographic location at determined times that the hypothetical observer will perceive solar glare from the potential source of glare, graphical data can be output that indicates to a user potential for ocular hazard at the times where glare is to be perceived. For example, the graphical data can include graphical objects that are rendered to indicate whether, for respective points in time, a human, at the location of the hypothetical observer, may potentially suffer permanent eye damage, after-image effects, or have low potential for after-image effects.

Accordingly, the technology described herein can be employed in connection with a proposed site for a solar installation or building or an existing solar installation to analyze potential for ocular hazard with respect to typical observer locations, such as along roadways, walking paths, or flight paths. In an example, a proposed site can be analyzed to determine if a driver on a roadway will be negatively impacted by glare from the potential source of glare. Furthermore, technology described herein can pertain to outputting suggested alterations in a current configuration of a solar installation and/or a proposed configuration of a solar installation. Such suggestions can be undertaken to reduce potential for ocular hazard for observers at specified locations. Still further, with respect to a solar power installation, an amount of energy to be harvested at the solar power installation can be predicted based upon a proposed configuration of the solar power installation and known weather patterns at the location of the proposed solar installation. A configuration of the solar installation can be automatically proposed that takes into consideration both the potential of ocular impact to observers as well as an amount of energy predicted to be harvested by the solar installation.

Other aspects will be appreciated upon reading and understanding the attached figures and description.

DETAILED DESCRIPTION

Figure 1:
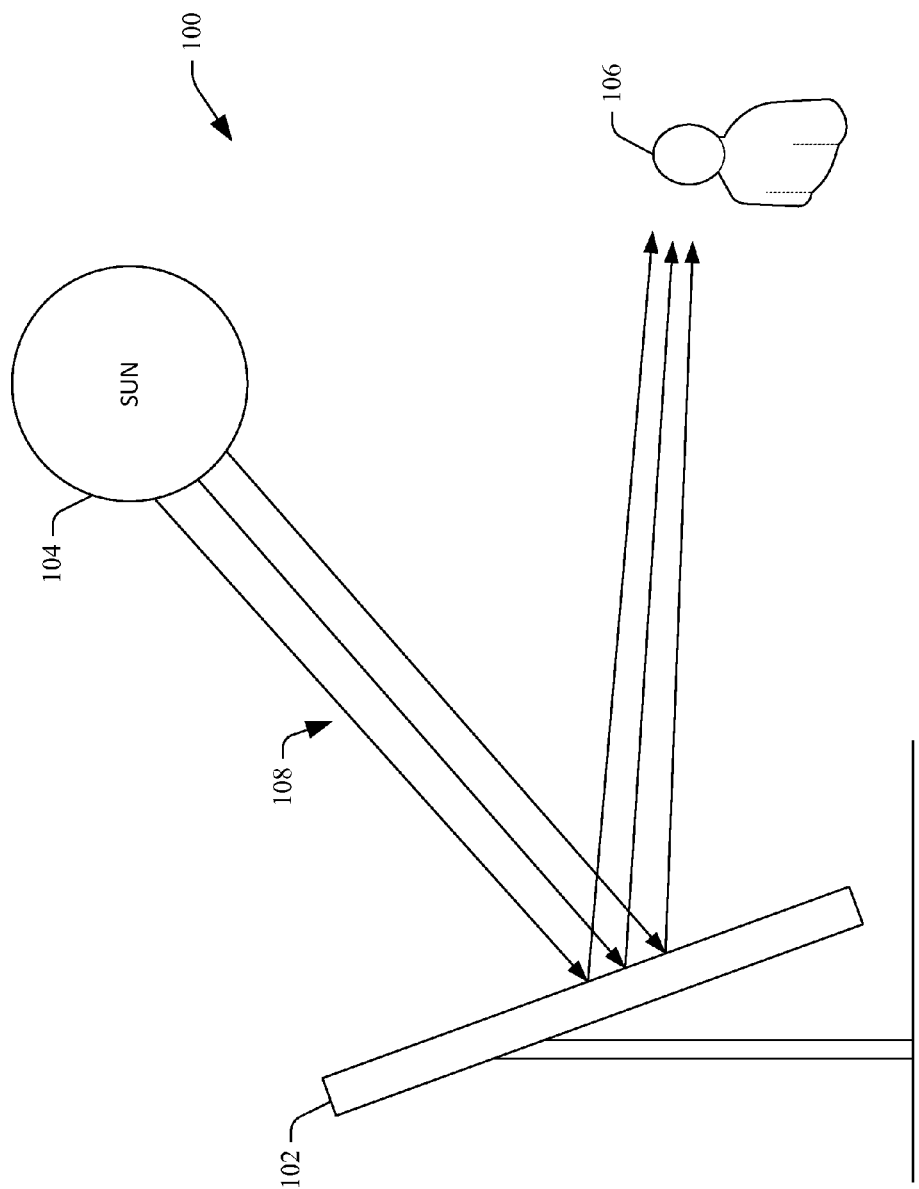
FIG. 1 is a diagram that illustrates an observer perceiving glare from a source of solar glare.

Various technologies pertaining to analyzing potential glint/glare hazards from a potential source of solar glare will now be described with reference to the drawings, where like reference numerals represent like elements throughout. In addition, several functional block diagrams of exemplary systems are illustrated and described herein for purposes of explanation; however, it is to be understood that functionality that is described as being carried out by certain system components may be performed by multiple components. Similarly, for instance, a component may be configured to perform functionality that is described as being carried out by multiple components. Additionally, as used herein, the term "exemplary" is intended to mean serving as an illustration or example of something, and is not intended to indicate a preference.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

With reference now to FIG. 1, an exemplary illustration 100 of an observer perceiving solar glare is illustrated. The illustration 100 comprises a potential source of solar glare 102. Pursuant to an example, the potential source of solar glare 102 may be a solar power installation or a portion thereof, such as a mirror used in connection with a concentrating power plant, a field of mirrors utilized in connection with a concentrating power plant, a photovoltaic module that includes a reflective coating (such as glass), a solar thermal receiver that is configured to receive concentrated solar radiation, etc. In another example, the potential source of glare 102 may be a structure, such as a vehicle or building that is composed of reflective materials such as mirrors, glass, or the like. The potential source of solar glare 102 is positioned at a first geographic location. Moreover, the potential source of solar glare 102 has some elevation above a reference plane, such as ground. While the potential source of solar glare 102 is shown in FIG. 1 as being relatively proximate to ground, it is to be understood that in some embodiments, the potential source of solar glare 102 can be positioned on top of existing structures, such as parking garages, buildings, etc. Furthermore, the potential source of solar glare 102 has a particular configuration, wherein the configuration includes a tilt angle (elevation angle) from a reference plane as well as an orientation (azimuthal angle) relative to a reference plane or direction, such as North. Such orientation, for instance, can define a direction that panels are facing. In an exemplary embodiment, the configuration of the potential source of solar glare 102 can be static. In other embodiments, the potential source of solar glare 102 may have actuators corresponding thereto that cause the tilt angle and/or orientation to change over the course of a day to track position of the Sun 104.

An observer 106 is located at a second geographic location and at a particular elevation above the reference plane. As shown in FIG. 1, radiation 108 emitted from the Sun 104 can impact the potential source of glare 102, reflect therefrom, and be directed towards the observer 106 when the observer 106 is at the second geographic location. Specifically, when the Sun 104 is at a particular position in the sky, the potential source of solar glare 102, given its location and configuration, reflects at least some of the radiation 108 towards an eye of the observer 106. In an example, when glare is emitted from the potential source of solar glare 102 (e.g., when the radiation 108 is reflected from the potential source of glare 102 and directed at the eye of the observer 106), the observer 106 may suffer ocular impact. The ocular impact may be temporary in nature such that the observer 106 experiences an after-image effect. In some instances, however, the observer 106 may suffer permanent ocular damage from the glare, such as retinal burn. Accordingly, it is desirable to configure the potential source of solar glare 102 such that humans in relatively high traffic areas, such as along roadways, flight paths, or air-traffic control towers are not subjected to relatively intense glare from the potential source of solar glare 102.

Figure 2:
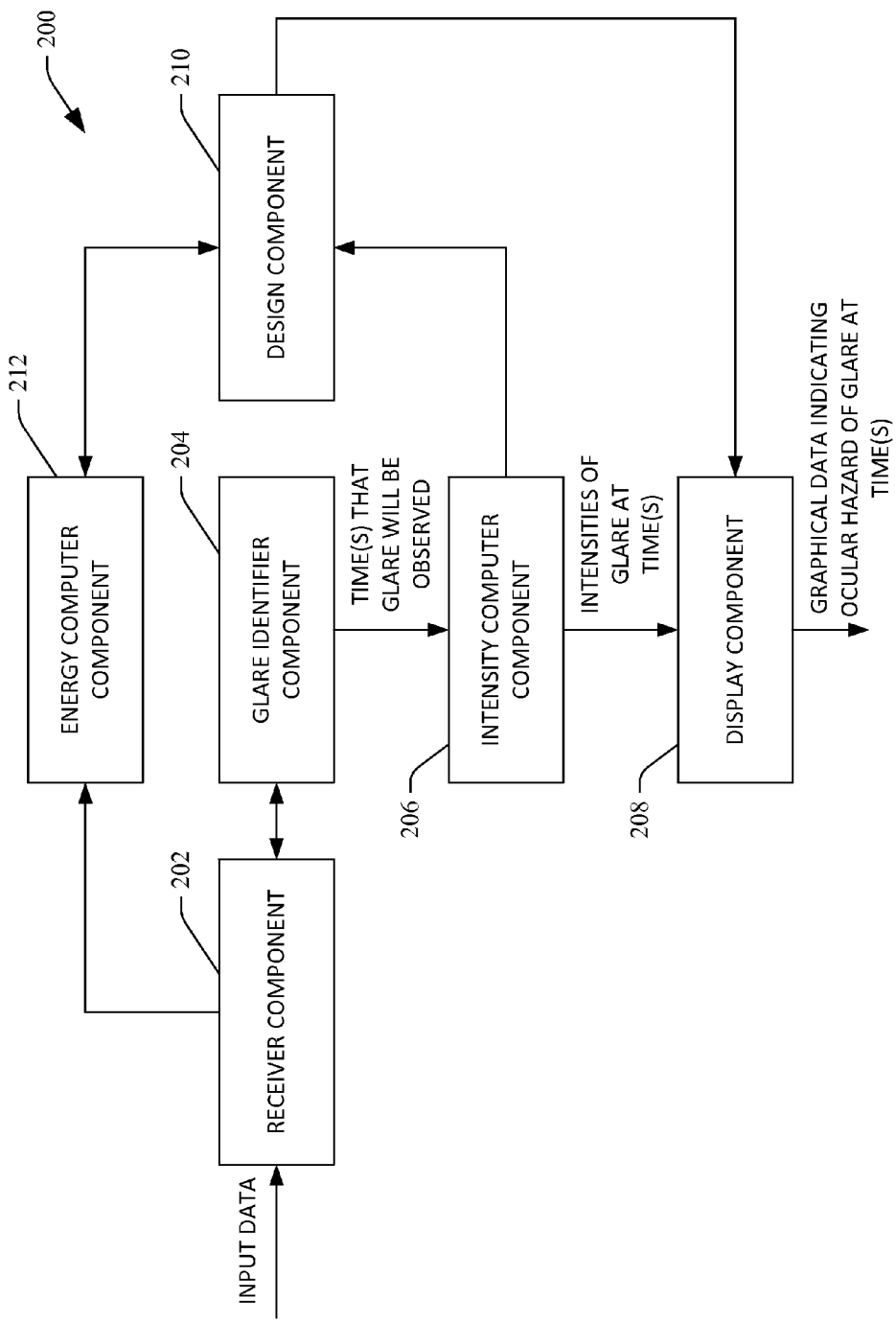
FIG. 2 is a functional block diagram of an exemplary system that facilitates analyzing potential ocular hazard corresponding to a potential source of solar glare.

With reference now to FIG. 2, an exemplary system 200 that facilitates analyzing potential ocular hazards corresponding to the potential source of glare 102 is illustrated. The system 200 can be a computer-executable system that operates in conjunction with a computer processor and memory. For example, the memory can include components of the system 200, and such components can be executed by the processor. In other embodiments, the system 200 or portions thereof can be implemented as an application specific integrated circuit, as a field programmable gate array, or the like.

The system 200 comprises a receiver component 202 that receives input data pertaining to the potential source of glare 102, the Sun 104, and the hypothetical observer 106. The input data received by the receiver component 202 can include, but is not limited to, first location data that is indicative of the first geographic location of the potential source of solar glare 102 (which can include the elevation of the potential source of solar glare 102), second location data that is indicative of the second geographic location of the hypothetical observer 106 of the solar glare from the potential source of solar glare 102, a value that is indicative of reflectivity of the potential source of solar glare 102, tilt angle (elevation angle) of the potential source of solar glare 102, orientation (azimuthal angle) of the potential source of solar glare 102, a slope error of the surface of the potential source of solar glare 102, solar time, Julian date, and latitude to define position of the Sun 104 (elevation and azimuth), data pertaining to parameters of the eye of the hypothetical observer 106, amongst other data.

As will be described in greater detail below, the receiver component 202 can receive the input data by way of a web-based user interface. Pursuant to a particular example, the receiver component 202 can receive at least a portion of the input data by way of user interaction with an interactive map. For example, the user can specify latitude/longitude coordinates of the potential source of solar glare 102 and the hypothetical observer 106 by employing a selection mechanism, such as a mouse, a touch sensitive display, or the like, to set forth an area that is to include the potential source of solar glare 102 and to set forth the location of the hypothetical observer 106. For instance, the user can specify the geographic location of the potential source of solar glare 102 in latitude/longitude coordinates by drawing a polygon (of arbitrary shape) on the interactive map. Likewise, the user can specify the geographic location of the hypothetical observer 106 by clicking a particular position in the interactive map or drawing a travel path of the hypothetical observer 106 in the interactive map.

The system 200 further comprises a glare identifier component 204 that is in communication with the receiver component 202 and identifies points in time that the hypothetical observer 106 will observe glare from the potential source of glare 102 when positioned at the second geographic location. The glare identifier component 204 identifies the aforementioned points in time based at least in part upon at least a portion of the input data received by the receiver component 202. For example, the glare identifier component 204 can identify the points in time where the hypothetical observer 106 will perceive glare when located at the second geographic location based at least in part upon the first location data that is indicative of the first geographic location of the potential source of glare 102 and the second location data that is indicative of the second geographic location of the hypothetical observer 106.

With more specificity, unit vectors can be defined, wherein the unit vectors initiate at each vertex of the polygon that defines the first geographic location and are directed to the second geographic location of the hypothetical observer 106. These unit vectors can be referred to herein as a view vectors. Subsequently, for each view vector, a specular reflected vector can be calculated from a normal vector of the potential source of solar glare 102 (normal vector) and each view vector, thereby obtaining a specular reflected unit vector (reflected view vector) that corresponds to a vertex of the polygon corresponding to the respective view vector. Subsequently, the glare identifier component 204 can calculate elevation (tilt angle) and azimuth angle (orientation) of the respective reflected view vector. The glare identifier component 204 can repeat such steps for each vertex of the polygon that defines the first geographic location of the potential source of solar glare 102.

Subsequently, the glare identifier component 204 can determine if the envelope created by the reflected view vectors from the vertices of the polygon encompasses a vector pointing from the source of solar glare 102 toward the Sun 104 (sun vector) at a particular time; if so, this would indicate the presence of glare at the location of the hypothetical observer 106 at that time. Alternatively, the sun vector and the normal vector can be used to calculate a reflected sun vector from the source of solar glare 102. The reflected sun vector is translated to the location of the observer 106 and reversed (pointing back toward the source of solar glare 102). If the reversed, translated, reflected sun vector intercepts the source of solar glare 102, then glare can be observed by the observer 106 at that particular time. The latter method can be used to indicate where glare will occur from the source of solar glare 102 at a particular time (e.g., in an animation). In an exemplary embodiment, the glare identifier component 204 can account for both the sun shape (4.7 mrad, which is half the subtended angle of the Sun 104) and beam spreading caused by the slope error of the reflective surface of the source of solar glare 102 (which causes scattering). The glare identifier component 204 can perform such actions for multiple positions of the Sun 104, and thus, for multiple different times over the course of the defined time range.

The system 200 further comprises an intensity computer component 206 that receives the times that glare will be observed by the hypothetical observer 106 at the second geographic location. Based upon the input data received by the receiver component 202, the intensity computer component 206 computes, for each point in time identified by the glare identifier component 206, a respective value that is indicative of intensity of the glare that will be observed by the hypothetical observer 106. The intensity of the perceived glare is understood herein to be a function of the retinal irradiance received at the observer location 106 and the subtended angle (size) of the glare visible on the source of solar glare 102. As will be described in greater detail herein, the intensity computer component 206 can compute values that are indicative of respective intensities of the glare at the points in time identified by the glare identifier component 204 based at least in part upon a reflectivity value that is indicative of reflectance of the potential source of glare 102. With more particularity, the input data received by the receiver component 202 can include an indication of material of the potential source of solar glare 102, and such indication can be employed to determine a reflectivity versus incidence angle. For the incidence angle of the Sun 104 relative to the surface normal of the potential source of solar glare 102, the intensity computer component 206 can calculate the reflectivity of the potential source of solar glare 102 based upon the reflectivity versus incidence angle function that corresponds to the material of the potential source of solar glare 102 or based upon a user-specified index of refraction (from Snell's Law). The intensity computer component 206, using equations set forth below and described with respect to FIGS. 9 and 10, can determine retinal irradiance and subtended angle of the Sun image reflected by the potential source of solar glare and can subsequently determine a potential level of ocular hazard (e.g. retinal burn, temporary after-image, low potential for ocular hazard).

The system 200 additionally comprises a display component 208 that receives the values that are indicative of respective intensities of glare observed by the hypothetical observer 106 at the times identified by the glare identifier component 204 and displays graphical data on a display screen of a computing device, wherein the graphical data comprises graphical objects that correspond to the respective intensity values computed by the intensity computer component 206. In an exemplary embodiment, the display component 208 can output a graph, wherein the graph can graphically depict times over the time range that glare will be observed by the hypothetical observer 106 at the second geographic location as well as indications of intensities corresponding to the glare at such times. For instance, the graph can include graphical objects located at positions in the graph to denote times that glare will be observed by the hypothetical observer 106, and such graphical objects can be rendered to indicate intensities of the glare observed by the hypothetical observer 106 at the times that glare is determined to occur, as well as potential ocular hazard to the hypothetical observer 106. For instance, color of a graphical object can indicate intensity or impact of glare. In another example, shape of a graphical object can indicate intensity or impact of glare observed by a particular hypothetical observer location, with multiple observer locations being possible for a given analysis.

The system 200 may further optionally include a design component 210 that receives intensity values for glare observed by the hypothetical observer 106 for various configurations of the potential source of solar glare 102 and outputs a suggestion as to configuration of the potential source of solar glare 102. In an example, a user of the system 200 can identify the first geographic location of the potential source of solar glare 102 but may fail to identify tilt angle and/or orientation of the potential source of solar glare 102. The system 200 can be configured to iterate through various configurations (tilt angles and orientations) to identify potential configurations that are not associated with relatively high levels of potential ocular hazard for specified observer locations. If, for example, the potential source of solar glare 102 is to be positioned near an airport or highway, it may be undesirable for observers along the highway to be impacted by glare from the potential source of solar glare 102. Accordingly, the design component 210 can identify configuration(s) of the potential source of solar glare 102 that cause low levels of ocular hazard to be perceived by those traveling the highway or flying via a flight path.

The system 200 may additionally optionally comprise an energy computer component 212 that can predict amounts of energy to be harvested by the potential source of solar glare 102 for differing configurations. The energy computer component 212 can undertake such predictions based upon historic weather patterns, known travel path of the Sun 104, materials utilized in the solar power installation, etc. Accordingly, if the first geographic location is set forth by a user of the system 200, the energy computer component 212 can predict amounts of energy that can be harvested from the potential source of solar glare 102 at various configurations of the potential source of solar glare 102.

The design component 210 may then receive predictions of energy harvest from the energy computer component 212 and can also receive corresponding glare intensity values from the intensity computer component 206. The design component 210 may then undertake a cost-benefit analysis, and can output one or more suggestions as to configuration (e.g., tilt angle, orientation, location) of the potential source of solar glare 102 that maximizes the overall benefit of the potential source of solar glare 102 (e.g. maximizes energy harvesting while effectively minimizing ocular hazard that may be caused by the potential source of solar glare 102).

Figure 3:
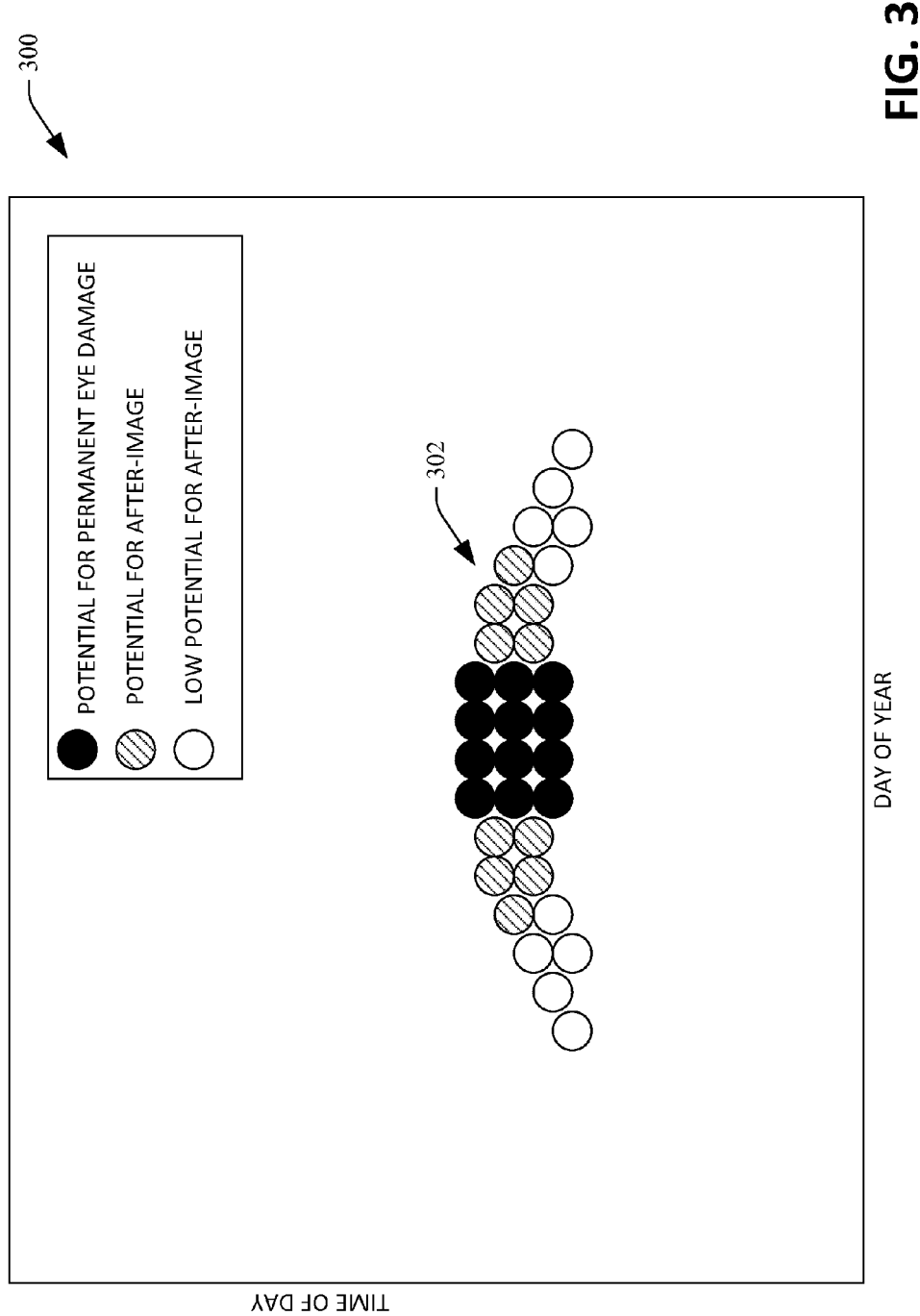
FIG. 3 illustrates an exemplary graphical depiction of potential ocular hazard caused by a potential source of solar glare.

With reference now to FIG. 3, an exemplary graph 300 that can be output by the display component 208 is illustrated. In the exemplary graph 300, an X axis is a specified timeframe provided to the receiver component 202, such as a month, two months, a year, or the like. The Y axis is time of day. The graph 300, in the example shown in FIG. 3, comprises a plurality of graphical objects 302, wherein the graphical objects 302 are located in the graph 300 to indicate times that the hypothetical observer 106 will perceive glare from the potential source of solar glare 102. The graphical objects 302 are rendered in the graph 300 based at least in part upon intensity values computed by the intensity computer component 206 for the times when glare is determined to be perceived by the hypothetical observer 106. For example, the graphical objects 302 can be rendered to indicate a level of potential ocular hazard that may be suffered by the hypothetical observer 106. Therefore, if a graphical object is rendered in a first color, a viewer of the graph 300 can ascertain that the potential ocular hazard for the hypothetical observer 106 is potential for permanent eye damage. Likewise, if a graphical object is rendered in a second color, a viewer of the graph 300 can ascertain that the glare (at the time in graph corresponding to the graphical object) may cause after-image to be experienced by the hypothetical observer 106. Additionally, if a graphical object is rendered in a third color, then a viewer of the graph 300 can ascertain that the glare from the potential source of solar glare 102 perceived by the hypothetical observer 106 is not likely to cause the hypothetical observer 106 to experience an afterimage effect.

While color has been described herein as a manner in which to visually indicate potential level of ocular hazard of the hypothetical observer 106, it is to be understood that the graphical objects can be rendered in other manners to differentiate between potential levels of ocular hazard as well as observation points. Furthermore, the levels of ocular hazard may be continuous rather than discrete so that, for example, a darker shade of red would indicate a higher potential for permanent eye damage. In another example, the graphical objects 302 can be rendered to indicate a difference between predicted retinal irradiance and retinal irradiance necessary to cause temporary afterimage effects for a given subtended angle divided by the difference of the retinal irradiance required to cause retinal burn and the retinal irradiance to cause afterimage (e.g., the log of each term, to linearize the scale). It is to be understood that the claims are not to be limited to a particular manner in which to display graphical data that is indicative of intensity of glare observed by the hypothetical observer 106.

Figure 4:
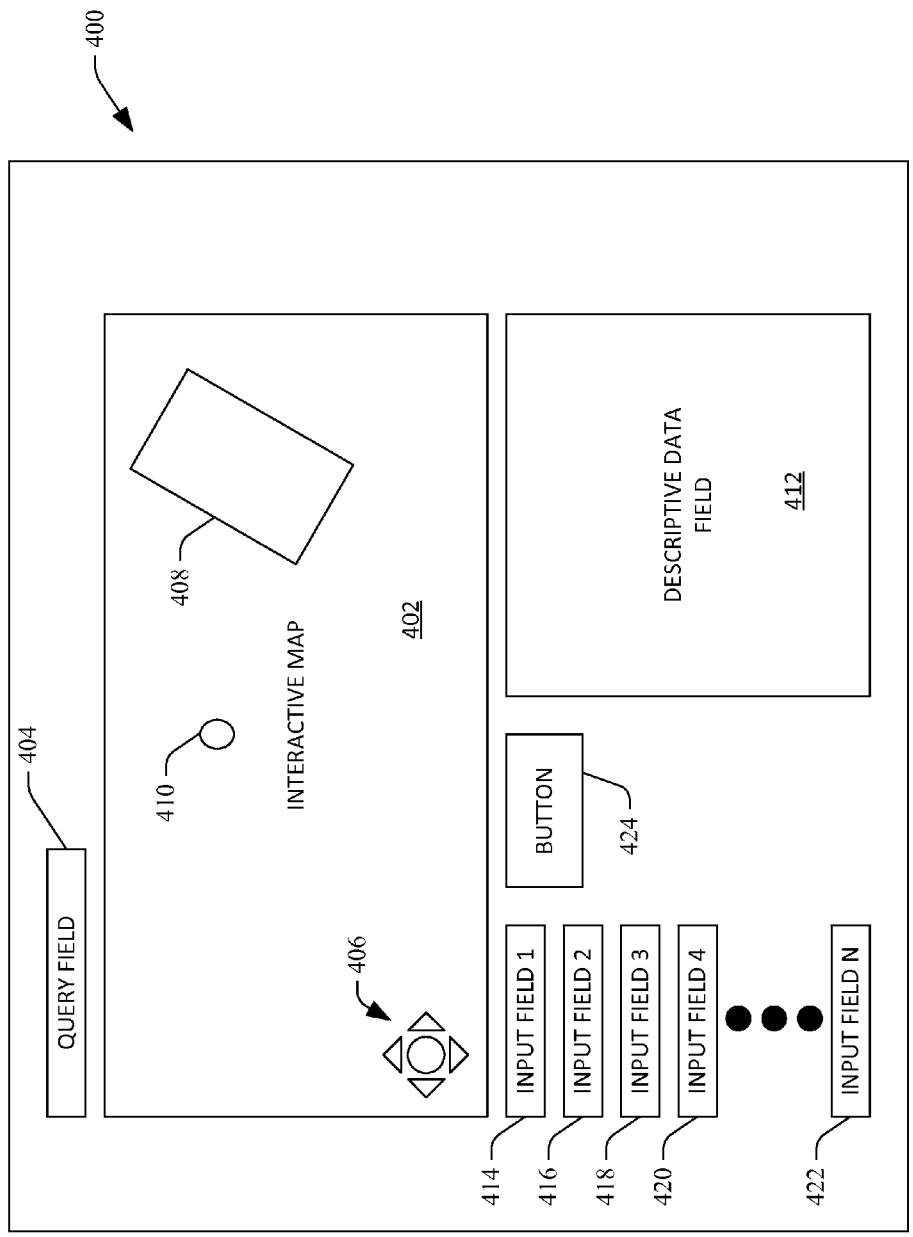
FIG. 4 is an exemplary graphical user interface that can be employed in connection with a tool that facilitates analyzing potential ocular hazard caused by a potential source of solar glare.

Now referring to FIG. 4, an exemplary graphical user interface 400 that can be employed by a user to interact with the system 200 shown in FIG. 2 is illustrated. In an exemplary embodiment, the graphical user interface 400 can be a web-based interface, such that a user can direct a web browser to a particular web page by entering a uniform resource locator (URL) into a field of the web browser, querying a search engine and selecting a search result corresponding to the graphical user interface 400, or other suitable manner for accessing the web-based graphical user interface. In another exemplary embodiment, the graphical user interface 400 can be an interface for a stand-alone application executing on a computing device.

A user of the graphical user interface 400 can employ the interactive map 402 to view a desired geographic region. Pursuant to an example, the graphical user interface 400 can include a query field 404 that can receive user input that is indicative of a desired geographic region that is shown in the interactive map 402. For example, the user can enter a name of a state, a city, a particular address, a landmark, an airport, etc., into the query field 404, and a geographic region can be displayed in the interactive map 402 based upon the data entered into the query field 404. Additionally, the interactive map 402 can comprise controls 406 that can be employed to navigate in numerous directions, alter elevation from the perspective of the user of the graphical user interface 400 (zoom in and zoom out), etc.

Once the desired geographic region is shown in the interactive map 402, the user of the graphical user interface 400 can define the first geographic location of the potential source of solar glare 102 (shown by reference numeral 408), and the second geographic location of the hypothetical observer 106 (shown by reference numeral 410). In an example, the user can define the first geographic region 408 by drawing a polygon on the interactive map 402, wherein the polygon defines boundaries of the potential source of solar glare 102. While in the graphical user interface 400 the first geographic location is shown as a rectangle, it is to be understood that the user can specify a polygon of any suitable shape in the interactive map 402 through utilization of, for example, a mouse, a touch-sensitive display, or the like. By drawing the polygon in the interactive map 402, the user is specifying latitude/longitude boundaries of the potential source of solar glare 102. Similarly, the user of the graphical user interface 400 can specify the second geographic location 410 of the hypothetical observer 106 by selecting a point on the interactive map 402. While the second geographic location 410 is shown as a single point, it is to be understood that the user of the interactive map 402 can define a travel path of the hypothetical observer 106 by way of clicking and/or dragging a path line. The elevation of the hypothetical observer 106 can be entered by the user or calculated by the system 202. As an example, the elevations along a flight path on final approach to a runway can be determined if the user specifies the landing location, flight path, and glide slope.

The graphical user interface 400 can additionally comprise a descriptive data field 412 that, for instance, can describe selections of geographic locations made by the user. For instance, the descriptive data field 412 can identify latitude/longitude coordinates of the first geographic location 408 and the second geographic location 410 selected by the user. Moreover, the descriptive data field 412 can set forth presumed data pertaining to the human eye, wherein such data is modifiable by the user.

The graphical user interface 400 additionally comprises a plurality of input fields 414-422. The input fields 414 through 422 can be configured to receive respective portions of the input data described above as being received by the receiver component 202. Accordingly, the input fields 414-422 can be configured to receive, but are not limited to receiving, orientation of the potential source of solar glare 102 (relative to a reference direction or plane), a tilt angle of the potential source of solar glare 102 (relative to a reference plane), a height of a centroid of the potential source of solar glare 102, a time range that is desirably analyzed, a slope error of the potential source of solar glare 102, a subtended angle of the Sun 104, a direct normal irradiance (DNI) value, and the like. Subsequent to the user selecting the first geographic location 408, the second geographic location 410, and providing appropriate data into the input fields 414-422, the user can select a button 424 on the graphical user interface 400, wherein selection of the button 424 causes the first geographic location 408, the second geographic location 410, and the data in the input fields 414-422 to be provided to the system 200. Responsive to receiving such data, the system 200 can be configured to output graphical data such as the graph shown in FIG. 3.

Figure 5:
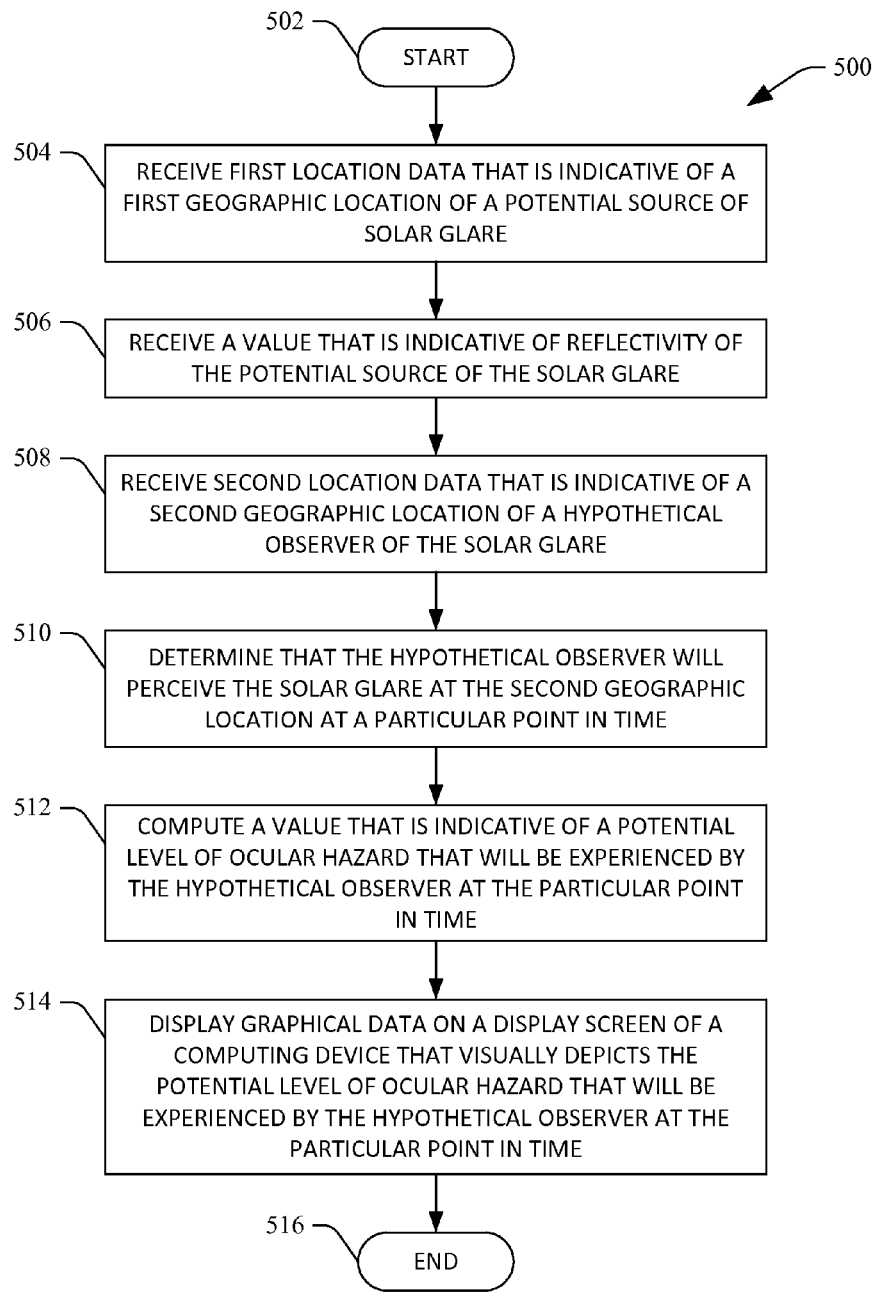
FIG. 5 is a flow diagram that illustrates an exemplary methodology for generating graphical data for display on a display screen of the computing device that visually depicts potential levels of ocular hazard that may be experienced by observers at different points in time with respect to a potential source of solar glare.
Figure 6:
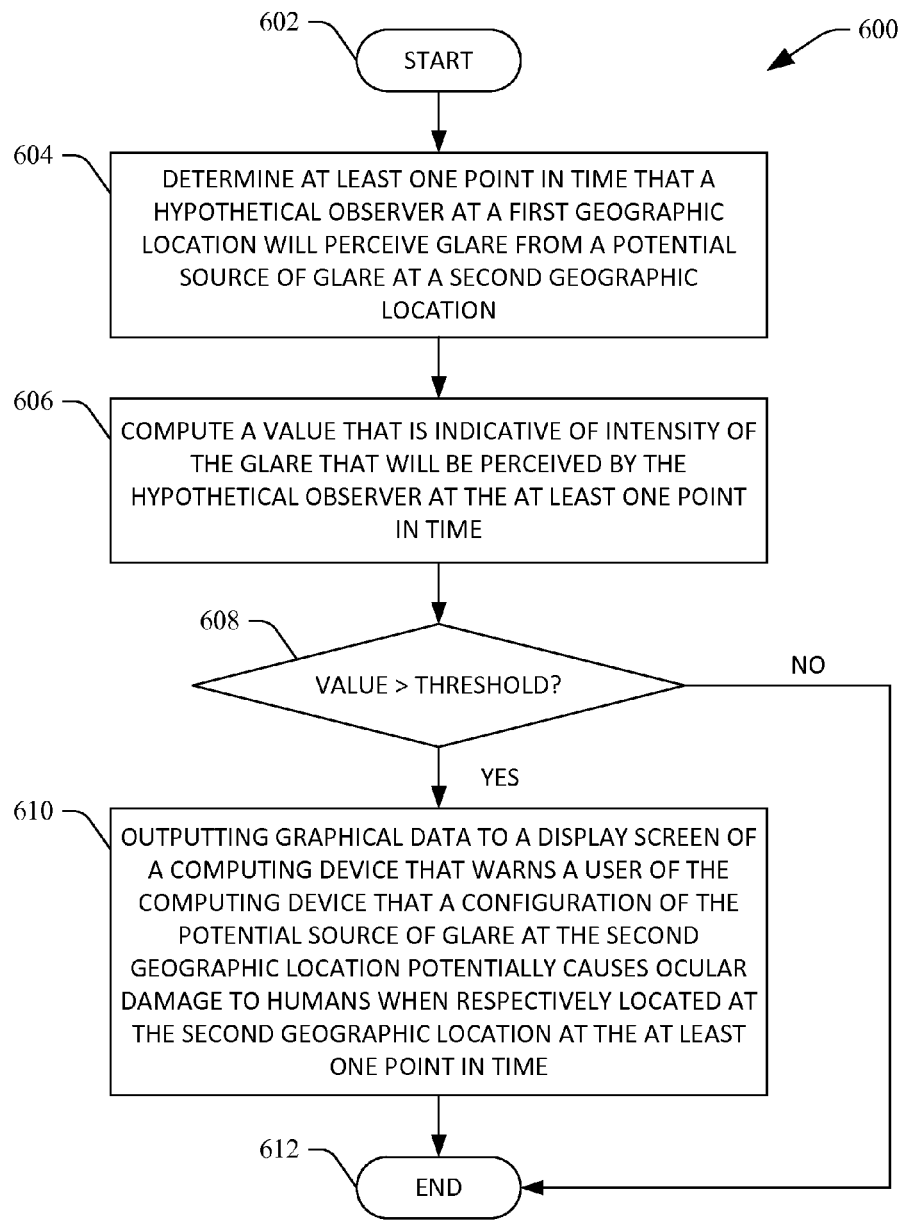
FIG. 6 is a flow diagram that illustrates an exemplary methodology that facilitates outputting graphical data to a display screen of a computing device that warns a user that the proposed configuration of a potential source of solar glare may potentially cause ocular damage to humans.
Figure 7:
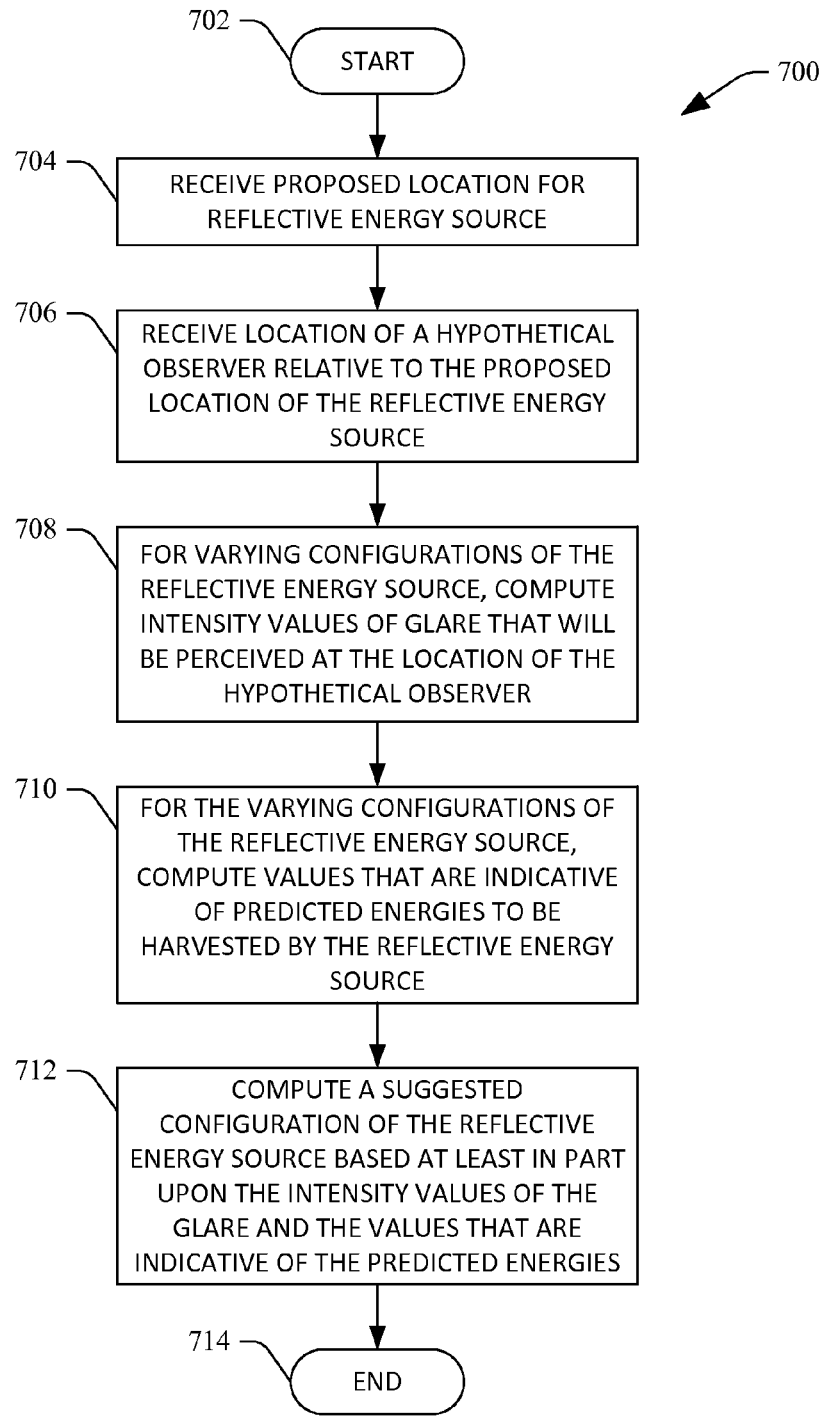
FIG. 7 is a flow diagram that illustrates an exemplary methodology for computing a suggested configuration of a potential source of solar glare based upon potential for the source of solar glare to cause ocular damage to humans at specified locations, as well as predicted amount of energy harvested by the potential source of solar glare with the configuration.

With reference now to FIGS. 5-7, exemplary methodologies are illustrated and described. While the methodologies are described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Moreover, the acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodologies may be stored in a computer-readable medium, displayed on a display device, and/or the like. The computer-readable medium may be any suitable computer-readable storage device, such as memory, hard drive, CD, DVD, flash drive, or the like. As used herein, the term "computer-readable medium" is not intended to encompass a propagated signal.

Now referring to FIG. 5, an exemplary methodology 500 that facilitates displaying graphical data on a display screen of a computing device that visually depicts potential levels of ocular hazard that will be experienced by a hypothetical observer at particular points in time is illustrated. The methodology 500 starts at 502, and at 504 first location data that is indicative of a first geographic location of a potential source of solar glare is received. At 506, a value that is indicative of reflectivity of the potential source of solar glare is received. At 508, second location data that is indicative of a second geographic location of the hypothetical observer of the solar glare is received.

At 510, a determination is made that the hypothetical observer will perceive glare from the potential source of solar glare when the hypothetical observer is at the second geographic location at a particular point in time. Such determination can be made based at least in part upon the first location data received at 504, the second location data received at 506, and a position of the Sun relative to the first geographic location at the particular point in time.

At 512, responsive to making the determination at 510, a value that is indicative of a potential level of ocular hazard that will be experienced by the hypothetical observer at the particular point in time is computed. Pursuant to an example, such value can be computed based at least in part upon reflectivity of the potential source of the solar glare.

At 514, graphical data is displayed on a display screen of the computing device that visually depicts the potential level of ocular hazard that will be experienced by the hypothetical observer at the particular point in time. It is to be understood that acts of the methodology 500 can be repeated for numerous points in time; for instance, acts 510-514 can be repeated for numerous points in time. The methodology 500 completes at 516.

With reference now to FIG. 6, an exemplary methodology 600 that facilitates outputting graphical data to a display screen of a computing device that warns a user of the computing device of a potential ocular hazard corresponding to a potential source of solar glare is illustrated. The methodology 600 starts at 602, and at 604 at least one point in time that a hypothetical observer at a first geographic location will perceive glare from a potential source of glare is determined, wherein the potential source of glare is at a second geographic location and has a specific configuration (elevation and azimuth angles). At 606, responsive to determining the at least one point in time, a value is computed that is indicative of intensity of the glare that will be perceived by the hypothetical observer at the at least one point in time. At 608, a determination is made regarding whether the value is above a threshold. If the value computed at 606 is above a threshold, then at 610 graphical data is output to a display screen of a computing device that warns the user of the computing device that the configuration of the potential source of solar glare at the second geographic location potentially causes ocular damage to humans when such humans are located at the first geographic location at the at least one point in time. Again, it is to be understood that one or more acts of the methodology 600 can be repeated for different points in time. If at 610 it is determined that the value is not above the threshold, then the methodology 600 completes at 612.

Now referring to FIG. 7, an exemplary methodology 700 that facilitates suggesting a configuration of a reflective energy source is illustrated. The methodology 700 starts at 702, and at 704 a proposed location for a reflective energy source is received. Such reflective energy source may be a field of photovoltaic modules, a field of mirrors used to concentrate solar radiation at a thermal collector, the thermal collector, or the like.

At 706, a location of a hypothetical observer relative to the proposed location of the reflective energy source is received. At 708, for varying configurations of the reflective energy source, intensity values of glare that will be perceived by hypothetical observer are computed. As described above, such intensity values can be computed for instances in time where the hypothetical observer will perceive glare from the reflective energy source.

At 710, for the varying configurations of the reflective energy source, values that are indicative of predictive energies to be harvested by the reflective energy source are computed. At 712, a configuration of the reflective energy source is suggested based at least in part upon the intensity values of the glare and the values that are indicative of the predicted energies. The methodology 700 completes at 714.

Additional details pertaining to computing the intensity values of glare are now provided. Such intensity values can be computed based upon two variables: 1) the retinal irradiance; and 2) the subtended angle (size) of a source of glare. The retinal irradiance can be calculated from the total power entering the pupil and the retinal image area. The diameter $d_r$ of the image projected onto the retina (assuming a circular image) can be determined from the sub-tended source angle $\omega$, which can be calculated from the source size $d_s$, radial distance r between the eye and the source, and the focal length of the eye (f=0.017 m), as follows:

$$d_r = f\omega, \text{ where } \omega = d_s/r. \quad (1)$$

If the irradiance at a plane in front of the cornea $E_c$ (W/m²) is known, power entering the pupil can be calculated as the product of the corneal irradiance in the pupil area (the daylight-adjusted pupil diameter $d_p$ is approximately 2 mm). The power can then be divided by the retinal image area, and multiplied by a transmission coefficient $\tau$ (~0.5), for the ocular media (to account for absorption of radiation within the eye before it reaches the retina) to yield the following expression for the retinal irradiance:

$$E_r = E_c(d_p^2/d_r^2)\tau. \quad (2)$$

In an example, retinal irradiance caused by viewing the Sun 104 directly can be calculated using Eq. (1) and Eq. (2) with $E_c$=0.1 w/cm², $d_p$=0.002 m, f=0.017 m, $\omega$=0.0094 rad, and $\tau$=0.5, which yields a retinal irradiance $E_r$~8 W/cm². It can be noted that the retinal irradiance is higher than the irradiance at the entrance of the eye. The calculated irradiances and thresholds used to determine ocular impacts can assume a standard solar spectral distribution, where the majority of the energy and short duration exposure impacts are due to radiation within the visible spectrum.

Figure 8:
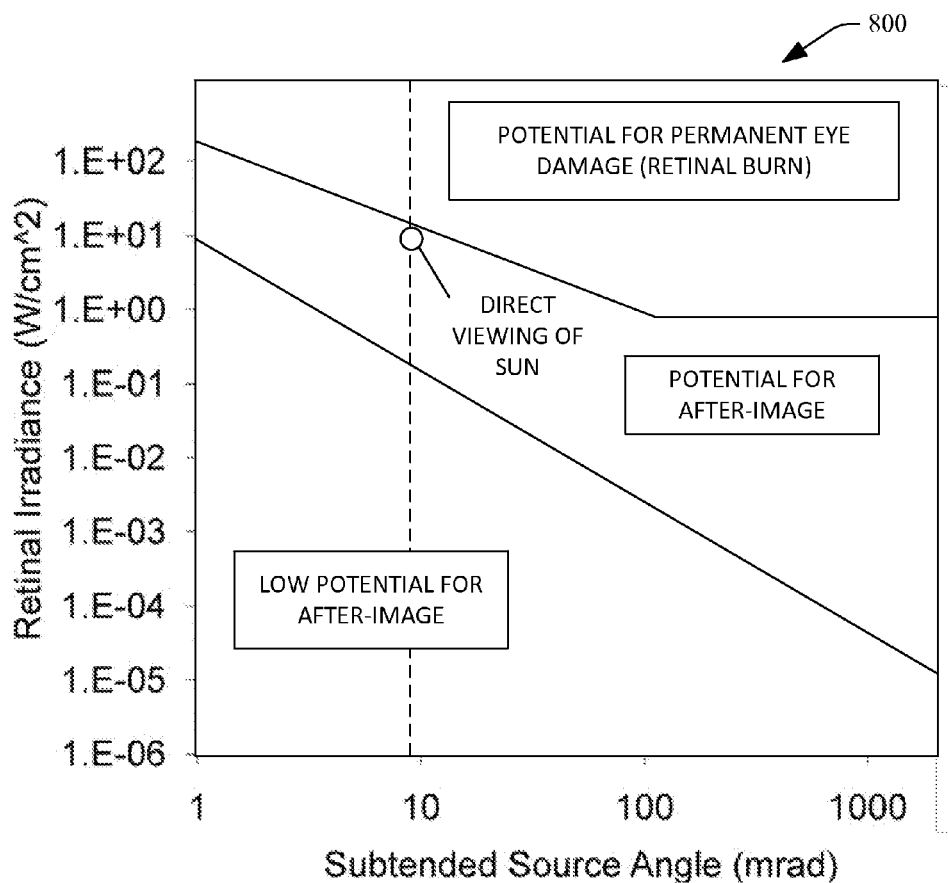
FIG. 8 illustrates a graph depicting potential levels of ocular hazard.

Turning briefly to FIG. 8, a graphical illustration 800 of potential impact of different retinal irradiances as a function of subtended source angle for short-term exposures are illustrated. Three regions are shown; 1) potential for permanent eye damage (retinal burn), 2) potential for temporary after-image (flash blindness), and 3) low potential for temporary after-image. If the retinal irradiance is sufficiently large for a given subtended source angle, permanent eye damage from retinal burn may occur. It can further be noted that as the subtended source angle increases, the safe retinal irradiance threshold decreases. Thus, for a given retinal irradiance, a larger subtended source angle can yield a larger retinal image area and can deliver a greater power to the retina that cannot be as easily dissipated from the parameter of the hot retinal image as with a smaller image area. In an exemplary embodiment, graphical objects in the graph 300 can be rendered in accordance with where in the graphical illustration 800 intensity values represented by the respective graphical objects lie.

Figure 9:
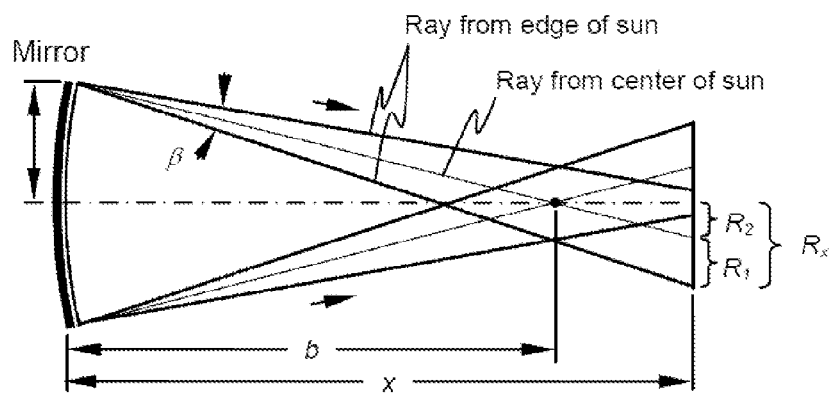
FIG. 9 illustrates reflectance of solar radiation from a mirror.

With reference to FIG. 9, geometry of specular solar reflections from a focused mirror is illustrated. An analytical model of beam irradiance resulting from specular solar reflections from a point-focus mirror can be derived with the following assumptions: (1) uniform Sun intensity; (2) round, focused, continuous surface mirrors; (3), no cosine losses, off-axis aberrations or atmospheric attenuation; and (4), uniform intensity in beam cross section.

These assumptions will generally produce the largest beam irradiance, but the assumption of uniform Sun intensity averages the intensity over the entire beam. Using a non-uniform solar intensity creates larger peak fluxes towards the center of the beam. Comparisons with a ray tracing model shows that the difference in peak fluxes about 25 to 30% at the focal length, but the difference can be greater at other distances.

The beam irradiance I [W/cm$^2$] may be calculated as the product of the direct normal irradiance, Q [W/cm$^2$], the mirror reflectivity $\rho$, and the area concentration ratio, C, as follows:

$$I = \rho Q C \qquad (3)$$

The direct normal irradiance, Q, at the Earth's surface is approximately 0.1 W/cm$^2$. The area concentration ratio C can be calculated as follows, assuming a circular mirror area, $A_h$, with radius, $R_h$, and a circular beam area, $A_x$, with radius, $R_x$, at a distance x from the mirror:

$$C = A_h/A_x = (R_h/R_x)^2. \qquad (4)$$

The radius, $R_x$, of the beam is comprised of two components:

$$R_x = R_1 + R_2, \qquad (5)$$

where $R_1$ is caused by the Sun angle and mirror contour inaccuracies (slope error) and $R_2$ represents focusing and defocusing characteristics of the beam at a distance that is less than or greater than the focal length. The beam divergence, $R_1$, at a distance x from the mirror is defined by the Sun half angle (approximately 4.7 mrad) and any additional slope errors caused by mirror inaccuracies:

$$R_1 \approx x \tan(\beta/2), \qquad (6)$$

where $\beta/2$ is the half angle of the total beam divergence. This approximation may have an error that is less than 0.3% for $b/R_h > 18$, where b is the focal length. $R_2$ can be defined as follows:

$$R_2/|x-b| = R_h/b \Rightarrow R_2 = |x/b-1| R_h. \qquad (7)$$

Using Eqs. (4), (5), (6), and (7) in equation (3) and the approximation that $\tan(\beta/2) = \beta/2$ when $\beta/2$ is small, yields the following expression for the beam irradiance [W/cm$^2$]:

$$I = \rho Q(x\beta/D_h + |x/b-1|)^{-2} \text{ (point-focus collector)} \qquad (8)$$

where $D_h = 2R_h$. The beam irradiance can also be presented in units of "Suns" by dividing Eq. (8) by Q~0.1 W/cm$^2$). The maximum beam irradiance occurs at the focal length x=b. In addition, the beam irradiance from a flat mirror can be calculated by setting b=∞ in Eq. (8). $D_h$ is the effective diameter of the mirror, which can be calculated from a total mirrored area of, for example, individual heliostats:

$$D_h = (4A_h/\pi)^{0.5}. \qquad (9)$$

As defined in Eq. (3), the irradiance is proportional to the concentration ratio, which is equal to the ratio of the measured irradiance at a given distance to the product of the direct normal irradiance, Q, and the mirror reflectivity. The concentration ratio is also equal to the area ratio of the mirror and the beam size. It follows that the relative spot size of the reflected image of the Sun and the mirror at a given distance is proportional to the measured irradiance at that location. Once the irradiance, I, is determined, the spot size of the reflected image of the Sun and the mirror can be estimated by the following equation assuming that the spot size is proportional to the irradiance:

$$A_{spot}/A_o = (d_{spot}/d_o)^2 = (x\omega_{spot}/x\beta)^2 =$$
$$C = I/\rho Q \Rightarrow \omega_{spot} = \beta\sqrt{I/\rho Q}, \qquad (10)$$

where A is the area of the reflected image on the mirror as viewed by an observer at a distance, x, away from the mirror; d is the diameter of the reflected image on the mirror; $\omega$ is the subtended angle of the reflected Sun image on the mirror (Sun angle plus slope error) as observed from a prescribed distance; $\beta$ is a beam divergence angle (Sun angle plus slope error); the subscript "spot" refers to the observed spot image on the mirror, and the subscript "o" refers to a nominal spot image of the Sun at an irradiance of one Sun times the mirror reflectivity ($\rho Q$), i.e., the spot size observed on a large flat mirror (b→∞, $D_h$→∞). Thus if the measure of irradiance I is greater or less than $\rho Q$, the observed size and subtended angle, $\omega_{spot}$, of the reflected spot image of the Sun will be greater or less than the nominal size and subtended angle, $\beta$, of the Sun image at a location x.

Using Eq. (10) in Eqs. (1) and (2) yields the following expression for the retinal irradiance, where a corneal irradiance, $E_c$, is set equal to irradiance I used in Eqs. (8) and (10):

$$E_r = \rho Q d_p^2 \tau/f^2 \beta^2. \qquad (11)$$

It can be noted that the retinal irradiance in Eq. (11) does not depend on distance from the source (assuming no atmospheric attenuation). As distance increases, both the power entering the pupil and the retinal image (which is proportional to the square of the subtended source angle) decrease at the same rate. Therefore, the retinal irradiance, which is equal to the power entering the pupil divided by the retinal image area, is independent of distance. The corneal irradiance, however, changes as a function of distance as given by Eq. (8).

The equations derived above with respect to determining the specular beam irradiance from point-focus collectors can be readily extended to line-focus (parabolic trough, linear Fresnel) collectors. The primary difference is that the concentration ratio in Eq. (4) is changed since the convergence/divergence of rays caused by the shape of the line focus mirror is primarily in one dimension (rather than two):

$$C = A_h/A_x = R_h/R_x. \qquad (12)$$

The resulting irradiance from the specular reflections from a line focus collector then becomes:

$$I = \rho Q(x\beta/D_h + |x/b-1|)^{-1} \text{ (line-focus collectors).} \qquad (13)$$

Eq. (13) is similar in form to Eq. (8) for point-focus collectors. However, the irradiance from line-focus collectors decreases less rapidly with distance past the focal point. Eq. (10) is still valid to describe the spot size of the reflected Sun image in the line-focus mirror. Using Eq. (10) and (13) in Eqs. (1) and (2) then yields the same expression for the retinal irradiance as Eq. (11) for point-focus collectors. The retinal irradiance is independent of distance, because the retinal image area decreases at the same rate as the irradiance, therefore the retinal irradiance can be constant.

Figure 10:
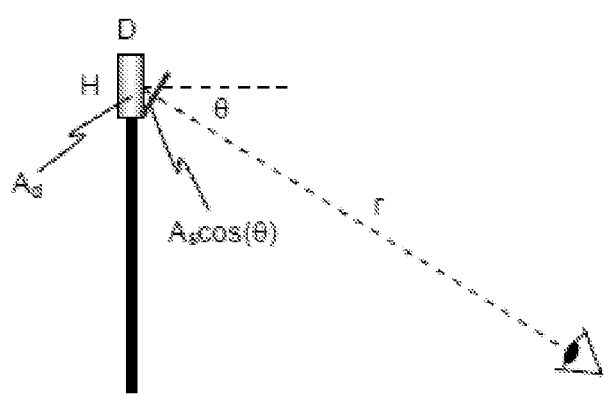
FIG. 10 illustrates solar radiation entering an eye of an observer.

An analytical model for diffuse reflections is now described. Reflections from receivers which are used to absorb the concentrated solar flux from heliostat, dish and trough collector systems can be modeled as diffuse rather than specular. Calculation of the irradiance at a location resulting from diffuse reflections depends on the total flux received by the reflecting source, reflectivity, size, and position of the source and distance to the source. First, the total power, $P_d$ emanating diffusely from the source is determined as follows:

$$P_d = (DNI) C(A_d) \rho \quad (14)$$

where DNI is the direct normal irradiance, C is the concentration ratio (Eq. (4)), $A_d$ is the surface area of the diffuse source, and $\rho$ is the reflectivity of the diffuse source. For a diffuse source, it can be assumed that the reflected radiance is uniform in all directions, yielding the following equation for diffuse irradiance, $I_d$ (W/m²), as a function of radial distance, r (m):

$$I_d = (P_d/\pi A_d)(A_s \cos(\theta)/r^2), \quad (15)$$

where the first term on the right-hand side of Eq. (15) is the diffuse reflected radiance [W/m²/sr], which is equal to the emissive flux $P_d/A_d$ divided by $\pi$. The radiance is multiplied by the solid angle subtended by the pupil of the eye. The radiance and solid angle are then multiplied by the ratio of the projected source area, $A_s \cos(\theta)$, and the pupil area to get the diffuse irradiance at the eye. The second term on the right-hand side of Eq. (15) is a product of the solid angle and the area ratio, where r is a radial distance of an observer relative to the source, $\theta$ is the angle between the surface normal and the line of sight between the source and the observer, and the pupil area cancels out. Note that as $\theta$ increases to 90°, the visible source area and the subtended solid angle go to zero. If the irradiating source is planar, then $A_d = A_s$. The potential for different areas of the diffuse source arise when a non-planar source exists, such as a cylindrical external central receiver. In this case, the diffuse source area, $A_d$, is equal to $\pi*D*H$, while the visible area, $A_s$, is approximately equal to $D*H$, where D is the diameter of the cylinder and H is the height. The projected area perpendicular to the line of sight is equal to $A_s \cos(\theta)$. Referring briefly to FIG. 10, a graphical representation of such parameters is illustrated.

Combining Eq. (15) with Eqs. (1) and (2) can yield the following expressions for the subtended angle, $\omega$ [rad], and diffuse retinal irradiance, $E_{r,d}$ [W/m²], where the corneal irradiance, $E_c$, in Eq. (2) is set to equal the diffuse irradiance, $I_d$, and the source size, $d_s$, is determined using Eq. (9) with $A_h = A_s \cos(\theta)$:

$$\omega = \sqrt{4 A_s \cos(\theta)/\pi}/r. \quad (16)$$

$$E_{r,d} = P_d d_p^2 \tau / 4 A_d f^2. \quad (17)$$

Using the aforementioned models that illustrate that retinal irradiance can be computed, and glint/glare intensity is a function of the retinal irradiance and the subtended source angle, the system 300 can compute the ocular impact of glint/glare emitted from a reflective entity.

Figure 11:
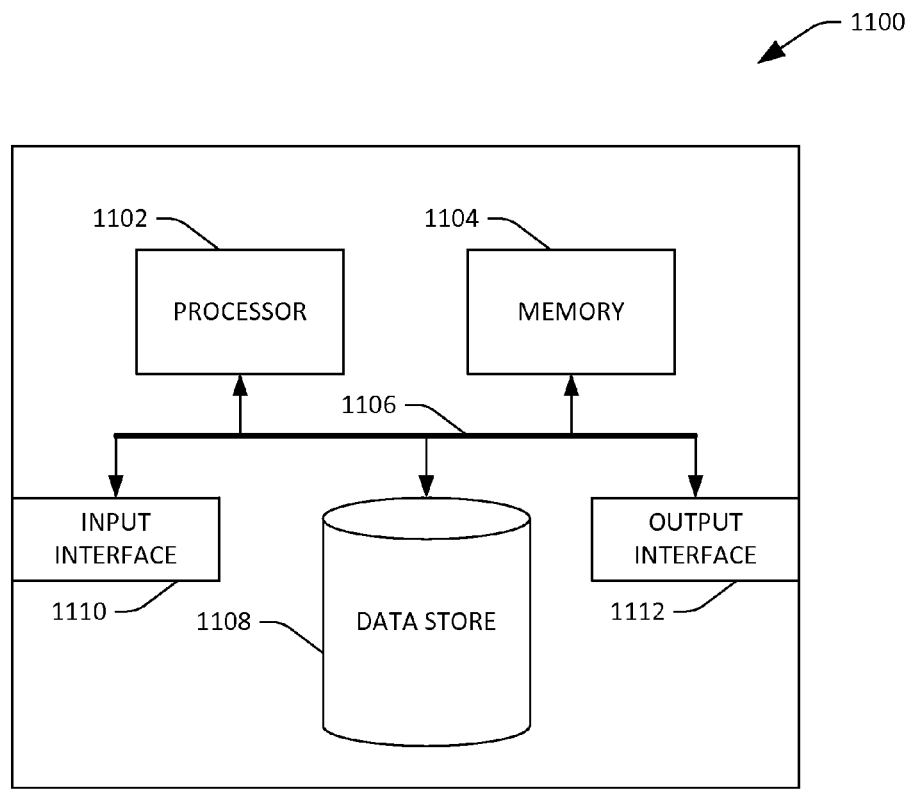
FIG. 11 is an exemplary computing device.

Now referring to FIG. 11, a high-level illustration of an exemplary computing device 1100 that can be used in accordance with the systems and methodologies disclosed herein is illustrated. For instance, the computing device 1100 may be used in a system that supports determining points in time that glare will be perceived by a hypothetical observer from a source of glare. In another example, at least a portion of the computing device 1100 may be used in a system that supports computing intensity of glare. The computing device 1100 includes at least one processor 1102 that executes instructions that are stored in a memory 1104. The memory 1104 may be or include RAM, ROM, EEPROM, Flash memory, or other suitable memory. The instructions may be, for instance, instructions for implementing functionality described as being carried out by one or more components discussed above or instructions for implementing one or more of the methods described above. The processor 1102 may access the memory 1104 by way of a system bus 1106. In addition to storing executable instructions, the memory 1104 may also store geographic coordinates, glare intensity values, etc.

The computing device 1100 additionally includes a data store 1108 that is accessible by the processor 1102 by way of the system bus 1106. The data store 1108 may be or include any suitable computer-readable storage, including a hard disk, memory, etc. The data store 1108 may include executable instructions, intensity values, received input values from a user, etc. The computing device 1100 also includes an input interface 1110 that allows external devices to communicate with the computing device 1100. For instance, the input interface 1110 may be used to receive instructions from an external computer device, a user, etc. The computing device 1100 also includes an output interface 1112 that interfaces the computing device 1100 with one or more external devices. For example, the computing device 1100 may display text, images, etc. by way of the output interface 1112.

Additionally, while illustrated as a single system, it is to be understood that the computing device 1100 may be a distributed system. Thus, for instance, several devices may be in communication by way of a network connection and may collectively perform tasks described as being performed by the computing device 1100. The computing device 1100 may also be a mobile computing device.

It is noted that several examples have been provided for purposes of explanation. These examples are not to be construed as limiting the hereto-appended claims. Additionally, it may be recognized that the examples provided herein may be permutated while still falling under the scope of the claims.

What is claimed is:

1. A method, comprising:
   receiving first location data that is indicative of a first geographic location of a potential source of solar glare;
   receiving a value that is indicative of reflectivity of the potential source of the solar glare;
   receiving second location data that is indicative of a second geographic location of a hypothetical observer of the solar glare;
   determining that the hypothetical observer will perceive the solar glare at the second geographic location at a particular point in time, wherein the determining is based at least in part upon the first location data, the second location data, and a position of the Sun relative to the first geographic location at the particular point in time;
   responsive to the determining that the hypothetical observer will perceive the solar glare at the second geographic location, computing a value that is indicative of a potential level of ocular hazard that will be experienced by the hypothetical observer at the particular point in time, wherein the value is computed based at least in part upon the value that is indicative of the reflectivity of the potential source of solar glare; and
   displaying graphical data on a display screen of a computing device that visually depicts the potential level of ocular hazard that will be experienced by the hypothetical observer at the particular point in time.

2. The method of claim 1, wherein the potential source of solar glare comprises at least one of a photovoltaic module, a mirror, a solar thermal receiver, or glass, the method further comprising:
   receiving a value that is indicative of beam spreading caused by at least one or sun shape or surface scattering; and computing the value that is indicative of a potential level of ocular hazard that will be experienced by the hypothetical observer at the particular point in time based at least in part upon the value that is indicative of the beam spreading.

3. The method of claim 1, wherein the first location data is indicative of latitude/longitude boundaries of the potential source of solar glare and elevation of the potential source of solar glare, and wherein the second location data is indicative of latitude/longitude position of the hypothetical observer and elevation of the hypothetical observer.

4. The method of claim 1, wherein the first location data and the second location data are received from a user by way of a computer-implemented interactive map of a geographic region that comprises the first geographic location and the second geographic location.

5. The method of claim 1, wherein the first location data the second location data, and the value that is indicative of the reflectivity of the potential source of solar glare are received by way of a web-based interface.

6. The method of claim 1, further comprising:
receiving an orientation of the potential source of solar glare relative to a reference orientation;
receiving a tilt angle of the source of solar glare relative to a reference plane;
computing the value that is indicative of the potential level of ocular hazard that will be experienced by the hypothetical observer at the particular point in time based at least in part upon the orientation of the potential source of solar glare and the tilt angle of the potential source of the solar glare; and
outputting at least one of an alternative orientation or an alternative tilt angle based at least in part upon the value that is indicative of the potential level of ocular hazard that will be experienced by the hypothetical observer at the particular point in time.

7. The method of claim 1, wherein the graphical data illustrates a plurality of locations in a geographic region where the glare will occur as a function of time.

8. The method of claim 1, wherein the potential source of solar glare comprises a module employed for energy production, and further comprising:
receiving a first orientation of the potential source of solar glare relative to a reference orientation;
receiving a first tilt angle of the potential source of solar glare relative to a reference plane;
computing the value that is indicative of the potential level of ocular hazard that will be experienced by the hypothetical observer at the particular point in tune based at least in part upon the first orientation of the potential source of solar glare and the first tilt angle of the potential source of solar glare; and
computing a predicted amount of energy to be produced by the potential source of solar glare for a specified time range based at least in part upon the first orientation of the potential source of solar glare and the first tilt angle of the potential source of solar glare.

9. The method of claim 8, further comprising:
receiving a second orientation of the potential source of solar glare relative to the reference orientation;
receiving a second tilt angle of the potential source of solar glare relative to the reference plane;
computing a second value that is indicative of the potential level of ocular hazard that will be experienced by the hypothetical observer at the particular point in time based at least in part upon the second orientation of the potential source of solar glare and the second tilt angle of the potential source of solar glare; and
computing a second predicted amount of energy to be produced by the potential source of solar glare for a specified time range based at least in part upon the second orientation of the potential source of solar glare and the second tilt angle of the potential source of solar glare;
comparing the value with the second value;
comparing the predicted amount of energy with the second predicted amount of energy; and
outputting a recommendation as to orientation and tilt angle of the potential source of solar glare based at least in part upon the comparing of the value with the second value and the comparing of the predicted amount of energy with the second predicted amount of energy.

10. The method of claim 1, wherein the second geographic location of the hypothetical observer is a potential travel path of the hypothetical observer.

11. The method of claim 1, wherein the graphical data displayed on the display screen comprises a graph, wherein the graph comprises a graphical object that is positioned in the graph to indicate the particular point in time, wherein the graphical object is rendered to visually depict the potential level of ocular hazard.

12. The method of claim 11, wherein the graphical object is assigned a color and/or shape to visually depict the potential level of ocular hazard from amongst a plurality of potential levels of ocular hazard and/or to visually depict a particular observation point from amongst a plurality of observation points.

13. A system, comprising:
a processor; and
a memory that is in communication with the processor, the memory comprising a plurality of components that are executed by the processor, the plurality of components comprising:
a receiver component that receives:
first location data that is indicative of a first geographic location of a potential source of glare;
second location data that is indicative of a second geographic location of a hypothetical observer;
a value that is indicative of reflectance of the potential source of glare;
a glare identifier component that identifies points in time that the hypothetical observer will observe glare when positioned at the second geographic location, the glare identifier component identifying the points in time based at least in part upon the first location data and the second location data; and
an intensity computer component that computes, for each point in time identified by the glare identifier component, a respective value that is indicative of intensity of the glare that will be observed by the hypothetical observer, the intensity computer component computing values indicative of respective intensities of the glare based at least in part upon the value that is indicative of the reflectance; and
a display component that displays graphical data on a display screen of a computing device, the graphical data comprising graphical objects that correspond to respective intensity values computed by the intensity computer component.

14. The system of claim 13 further comprising a server that is accessible by way of a web browser.

15. The system of claim 14, wherein the receiver component receives the first location data and the second location data by way of user-interaction with an interactive map of a geographic region that comprises the first geographic location and the second geographic location.

16. The system of claim 15, wherein the first location data is received responsive to a user specifying a polygon on the interactive map, the polygon identifying the first geographic region.

17. The system of claim 13, wherein the intensity computer component additionally identifies potential levels of ocular hazard that respectively correspond to the intensity values, and wherein the graphical objects are rendered in accordance with respective levels of ocular hazard corresponding thereto.

18. The system of claim 13, further comprising a design component that outputs at least one of a suggested orientation of the potential source of glare relative to a reference orientation or a suggested tilt angle of the potential source of glare relative to a reference plane, wherein a risk of ocular hazard of the hypothetical observer is reduced when the potential source of glare is configured at at least one of the suggested orientations or the suggested tilt angles relative to when the potential source of glare is configured at another orientation or tilt angle.

19. The system of claim 18, wherein the design component outputs the at least one of the suggested orientation or the suggested tilt angle based at least in part upon an expected amount of energy cultivated from the potential source of glare when configured at at least one of the suggested orientation or the suggested tilt angle.

20. A non-transitory computer-readable data storage device comprising instructions that, when executed by a processor, cause the processor to perform acts comprising:
  determining at least one point in time that a hypothetical observer at a first geographic location will perceive glare form a potential source of glare at it second geographic location, the potential source of glare having a specified configuration;
  responsive to determining the at least one point in time, computing a value that is indicative of intensity of glare perceived by the hypothetical observer at the at least one point in time;
  determining that the value lies above a pre-defined threshold value; and
  responsive to determining that the value lies above the pre-defined threshold value, outputting graphical data to a display screen of a computing device that warns a user of the computing device that the configuration of the potential source of glare at the second geographic location potentially causes ocular damage to humans when positioned at the second geographic position at the at least one point in time.

* * * * *